United States Patent [19]

Kenna

[11] Patent Number: 4,718,911
[45] Date of Patent: Jan. 12, 1988

[54] ACETABULAR CUP ASSEMBLY

[75] Inventor: Robert V. Kenna, Saddle River, N.J.

[73] Assignee: Pfizer Hospital Products Group Inc., New York, N.Y.

[21] Appl. No.: 831,246

[22] Filed: Feb. 19, 1986

[51] Int. Cl.$^4$ .............................................. A61F 2/34
[52] U.S. Cl. .................................................. 623/22
[58] Field of Search ...................... 623/18, 19, 20, 21, 623/22, 23; 403/135, 140, 122

[56] References Cited

U.S. PATENT DOCUMENTS

| | | | |
|---|---|---|---|
| 3,656,184 | 4/1972 | Chambers | 623/23 |
| 3,813,699 | 6/1974 | Giliberty | 623/23 |
| 3,818,512 | 6/1974 | Shersher | 623/23 |
| 3,863,273 | 2/1975 | Averill | 623/23 |
| 3,938,198 | 2/1976 | Kahn et al. | 623/23 |
| 3,982,281 | 9/1976 | Giliberty | 623/23 |
| 4,030,143 | 6/1977 | Elloy et al. | 623/23 |
| 4,044,403 | 8/1977 | D'Errico | 623/23 |
| 4,159,544 | 7/1979 | Termanini | 623/23 |
| 4,172,296 | 10/1979 | D'Errico | 623/23 |
| 4,241,463 | 12/1980 | Khovaylo | 623/23 |
| 4,380,090 | 4/1983 | Ramos | 623/23 |
| 4,408,360 | 10/1983 | Keller | 623/23 |
| 4,410,295 | 10/1983 | Ersoy et al. | 403/135 |
| 4,619,658 | 10/1986 | Pappas et al. | 623/22 |

Primary Examiner—Richard J. Apley
Assistant Examiner—David J. Isabella
Attorney, Agent, or Firm—Peter C. Richardson; Lawrence C. Akers; Mark Dryer

[57] ABSTRACT

A three-component acetabular cup assembly for receiving and releasably retaining the femoral head component of a prosthesis, said cup assembly comprising an outer metal shell, a cup-shaped inner bearing of substantially rigid plastic fixedly secured within said metal shell, and a locking ring made from the same plastic as the inner bearing; the outer surface of the bearing and the inner surface of the locking ring having cooperating configurations forming a secure but releasable latch.

6 Claims, 6 Drawing Figures

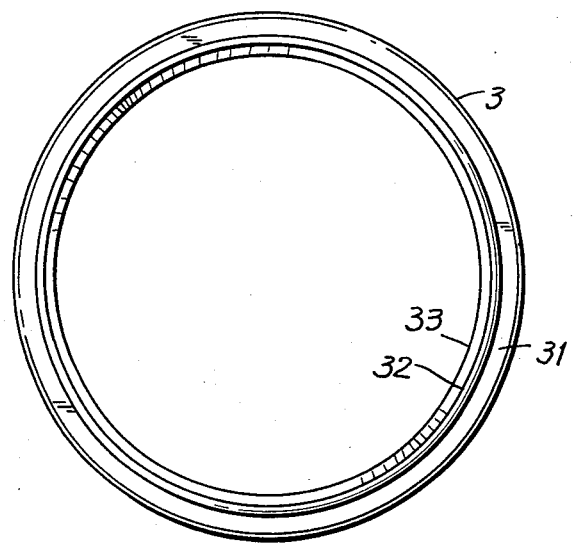
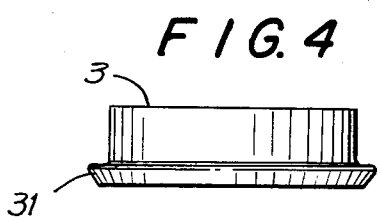
FIG. 3
FIG. 4
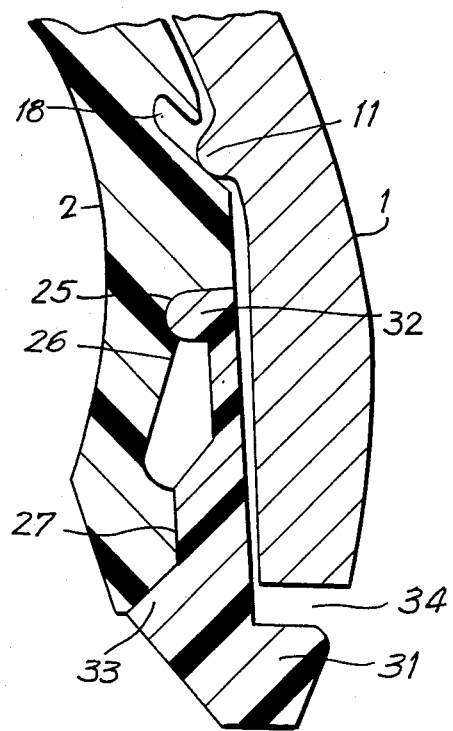
FIG. 5

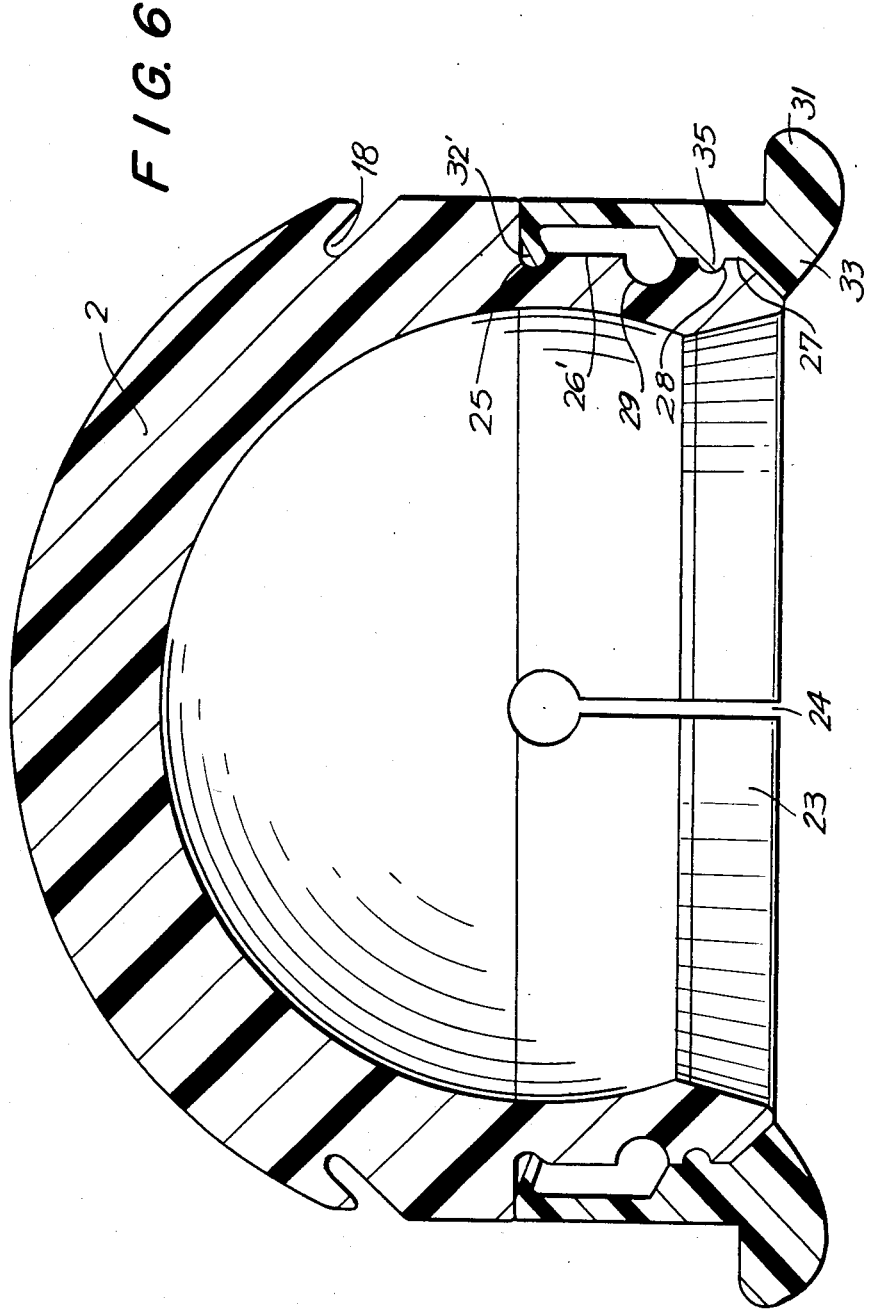

ACETABULAR CUP ASSEMBLY

BACKGROUND OF THE INVENTION

This invention relates to an acetabular cup assembly for an artificial hip prosthesis. More particularly, the invention is concerned with a three-component acetabular cup assembly for receiving and releasably retaining the femoral head component of a prosthesis.

Artificial hip-joints comprising an endoprosthesis of an acetabulum and an endoprosthesis of a femur are known in the art.

In such prior art prostheses various means for accommodating and retaining the femoral head within the acetabular cup or socket have been disclosed.

For example, U.S. Pat. No. 3,813,699 discloses a hip-joint prosthesis comprising a cup member adapted to snap in place over and holdingly engage a spherical femoral head member. U.S. Pat. No. 3,982,281 discloses a modification of the prosthesis described in U.S. Pat. No. 3,813,699.

U.S. Pat. Nos. 3,863,273; 4,044,403 and 4,172,296 disclose prosthetic hip-joints having various arrangements for retaining the femoral head within the socket member.

U.S. Pat. No. 4,241,463 discloses a prosthetic joint wherein the femoral head is retained within a bearing insert by movement of a split locking ring located intermediate the bearing and the ball-shaped femoral head.

Other arrangements for retaining the femoral head in ball-and-socket joint prosthesis are disclosed in U.S. Pat. Nos. 3,656,184; 3,938,198; 4,030,143; 4,159,544; 4,380,090 and 4,408,360.

U.S. Pat. No. 3,818,512 discloses an artificial hip-joint wherein a femoral head member is locked into an insert member installed within a fixed acetabulum prosthesis, said insert member being screwably fixed into said acetabulum by a self-locking nut.

The above references, which are merely representative, are indicative of the extensive interest in the art to provide successful hip-joint prostheses and, in particular, to provide ball and socket joints which provide maximum articulation and minimum dislocation.

However, none of the prior art prostheses have addressed and successfully resolved the problem not only of retaining the head in the socket but also of easily releasing the head, when required, without impairing the locking facility.

The present invention provides a neat solution to the aforesaid problem by an acetabular cup assembly comprising components having a unique inter-locking and releasable interaction with each other.

SUMMARY OF THE INVENTION

In accordance with the invention there is provided a three-component acetabular cup assembly for receiving and releasably retaining the femoral head component of a prosthesis, said cup assembly comprising:

a metal shell defining an opening about a peripheral edge adapted to removably fit within the natural anatomical acetabulum;

a cup-shaped inner bearing of substantially rigid plastic fixedly secured within said opening of said metal shell, the inner surface of said bearing being substantially hemispherical with a cylindrical apron and adapted to accept said femoral head, said apron having a plurality of resilient leaves formed by longitudinal slits extending to a distal end, whereby said leaves are adapted to move outwardly to allow passage of said femoral head into said inner bearing, the outer surface of said bearing having a groove running circumferentially around the apron, and a circumferential ridge adjacent said groove, and the distal end of each leaf terminating in an outwardly projecting lip; and a locking ring made from the same plastic as the inner bearing and having a substantially cylindrical configuration terminating in an outwardly projecting lip which overlaps the peripheral edge of said metal shell in the locked position, the inner wall of said ring having inwardly projecting first and second flanges, said first flange being adapted to pass over said circumferential ridge in said inner bearing in order to snap into said groove while said second flange butts against the distal end of each leaf when said locking ring is pushed over the outer wall of said inner bearing, preventing the leaves of said bearing from moving outward and thereby releasably locking said bearing around said femoral head, there being an annular gap left between said lip of the locking ring and the adjacent periphery of the metal shell, whereby said prosthesis may be readily disassembled by prying said lip away from said shell periphery.

The inner bearing of the cup assembly of the invention is made from a substantially rigid plastics material, herein referred to by the simple colloquial term "plastic". The plastic is not only substantially rigid but also should be sufficiently resilient to allow the leaves in the apron to move outwardly and inwardly without cracking or breaking. Also a certain degree of resilience is required in the locking ring to allow it to snap into locking engagement with the inner bearing and to be pryed away therefrom as described above. Additionally, the inner surface of the bearing should be of such a nature that there is negligible friction between said surface and the material, usually metal, of the femoral head. A plastic which possesses these desired characteristics is ultra high molecular weight (UHMW) polyethylene and this is the preferred plastic for the inner bearing and locking ring of the present invention. Other plastics having the desired characteristics are known in the art and may be used in the present invention, for example polyfluoroethylene and silicone.

The metal of the metal shell may be any biologically-inert, corrosion-resistant metal alloy known in the art for endoprostheses. A particularly suitable and preferred metal is the high strength chromium-cobalt-molybdenum alloy known by the Registered Trade Mark "Vitallium".

In a preferred embodiment of the invention the metal shell is not fixed to the patient's acetabulum but is adapted to move in a substantially frictionless manner within the acetabulum so that the resultant joint is capable of articulation not only between the femoral head and inner bearing but also between the total hip prosthesis and the natural anatomical acetabulum. This type of acetabular prosthesis is known in the art as a bi-polar cup. To allow said movement within the acetabulum, the outer surface of the metal shell is preferably highly polished.

In a particularly preferred embodiment of the invention the first flange of the locking ring is a circular flap which lockingly engages with the groove in the inner bearing and the inner surface of the locking ring has an additional convex flange, located above said second flange, which convex flange engages with a cooperating concave groove in the outwardly projecting lip at the distal end of each leaf of said inner bearing.

BRIEF DESCRIPTION OF THE DRAWINGS

Two embodiments of the invention are illustrated in the accompanying drawings in which:

FIG. 3 is a top plan view of the locking ring;

FIG. 4 is a side elevation of the locking ring;

FIG. 5 is an enlarged sectional view of the locking ring in locked position around the inner bearing; and FIG. 6 is an enlarged sectional view of an alternative embodiment in which the outer surface of the inner bearing and the inner surface of the locking ring have different profiles from the embodiment of FIGS. 1–5.

DETAILED DESCRIPTION OF THE INVENTION

Figure 1:
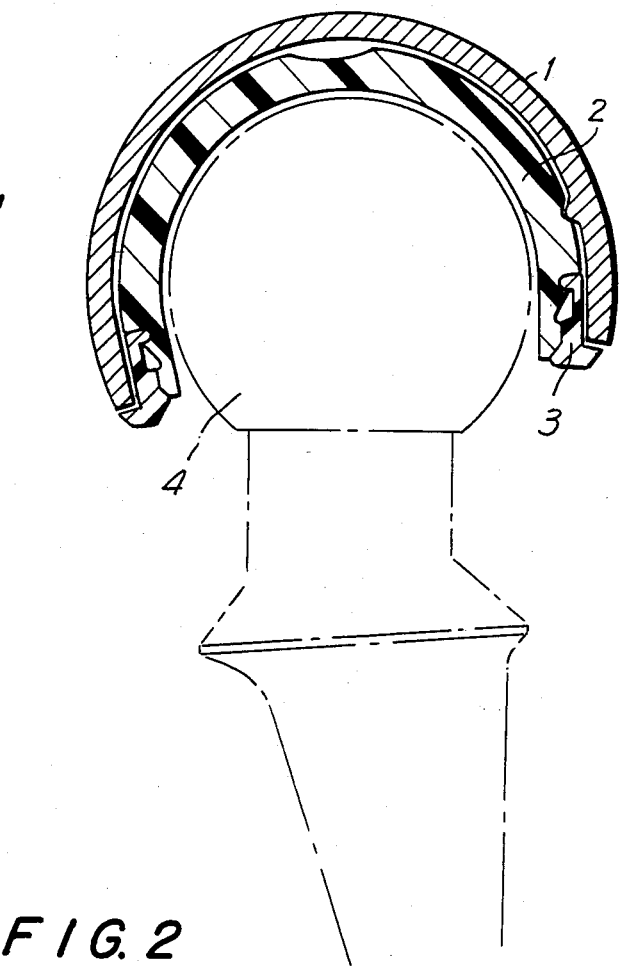
FIG. 1 is a side elevation of a prosthesis showing a sectional view of the acetabular cup assembly.

Referring to the first embodiment illustrated in the drawings, FIG. 1 illustrates an acetabular cup assembly comprising a metal shell 1, within which is fixedly secured an inner bearing 2. A locking ring 3 is in position around the inner bearing and releasably locks the bearing around a femoral head 4.

Figure 2:
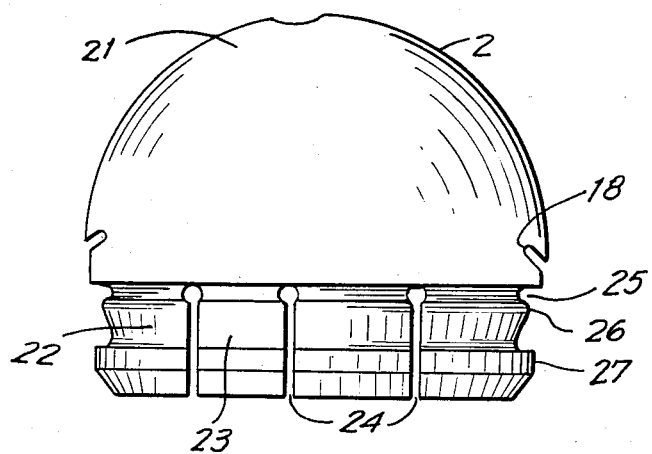
FIG. 2 is a side elevation of the inner bearing.

Referring to FIG. 2, the inner bearing comprises a substantially hemispherical portion 21 and a cylindrical apron 22. The apron has a plurality of resilient leaves 23 formed by longitudinal slits 24. The leaves are adapted to move outwardly to allow passage of the femoral head into the inner bearing and also, when desired, to allow removal of the femoral head. However, outward movement of the leaves is prevented when the locking ring is snapped into position as described hereinafter.

The outer surface of the bearing has a groove 25 running circumferentially around the apron and a circumferential ridge 26 adjacent said groove. The ridge is a section of increased diameter which decreases sharply to form the groove 25 at its top end and slopes gradually inwardly towards its lower end terminating in another section of increased diameter forming an outwardly projecting lip 27 at the distal end of each leaf.

The inner bearing is fixedly secured within the metal shell with aid of a circumferential notch 18 which lockingly engages with an appropriate lip or flange 11 (FIG. 5) on the inner surface of the metal shell. Any other suitable means may be used for the locking engagement of the bearing within the shell.

Referring to FIGS. 3, 4 and 5, the locking ring 3 has a substantially cylindrical configuration terminating in an outwardly projecting lip 31 which overlaps the peripheral edge of the metal shell 1 in the locked position illustrated in FIG. 1 and FIG. 5.

The inner wall of the locking ring has a first flange 32 and a second flange 33. The first flange is adapted to pass over the circumferential ridge on the outer surface of the inner bearing in order to snap into the groove 25 when the locking ring is pushed over the outer wall of the inner bearing to the locked position. To ensure a secure latch the configuration of the male flange 32 should preferably matchingly conform to the female groove 25. Thus, in the illustrated first embodiment the groove 25 is a full round concave and the flange 32 is a full round convex of the same radius.

In the locked position the second flange 33 of the locking ring butts against the distal end of each leaf. Accordingly, to ensure a close-fitting touching engagement the inner profile of the flange should match the outer profile of the projecting lip 27 at the distal end of each leaf. The resulting close engagement prevents the leaves from moving outwardly and locks the inner bearing around the femoral head To allow simple and quick release of the femoral head, when desired, an annular gap 34 is provided between the lip 31 and the adjacent periphery of the metal shell 1. The prosthesis may be readily disassembled by prying the lip 31 away from the shell periphery using a suitable tool (not shown) inserted in the annular gap.

FIG. 6 illustrates an alternative and particularly preferred embodiment in which the inner surface of the locking ring has an additional convex flange 35, located just above the second flange, which convex flange engages with a cooperating concave groove 28 set in the projecting lip 27 of the inner bearing. Additionally, the first flange 32' of the locking ring is a circular flap which lockingly engages with the groove 25 in the inner bearing. Also the ridge 26' in this embodiment is of substantially the same diameter throughout its length and terminates in a further convex groove 29 at its lower end. The other features of this embodiment are similar to and have the same reference numerals as like features in the embodiment of FIGS. 1–5.

The cup assembly of the present invention, as exemplified by the illustrated embodiments provides a prosthesis which is secure against inadvertent dislocation but is adapted for easy disassembly when required.

I claim:

1. A three component acetabular cup assembly for receiving and releasably retaining the femoral head component of a prosthesis, said cup assembly comprising:

a metal shell defining an opening about a peripheral edge and adapted to removably fit within the natural anatomical acetabulum;

a cup-shaped inner bearing of substantially rigid plastic fixedly secured within said opening of said metal shell, the inner surface of said bearing being substantially hemispherical with a cylindrical apron and adapted to accept said femoral head, said apron having a plurality of resilient leaves formed by longitudinal slits extending to a distal end, whereby said leaves are adapted to move outwardly to allow passage of said femoral head into said inner bearing, the outer surface of said bearing having a groove running circumferentially around the apron, and a circumferential ridge adjacent said groove, the distal end of each leaf terminating in an outwardly projecting lip; and a locking ring made from the same plastic as the inner bearing and having a substantially cylindrical configuration terminating in an outwardly projecting lip which overlaps the peripheral edge of said metal shell in the locked position, the inner wall of said ring having inwardly projecting first and second flanges, said first flange being adapted to pass over said circumferential ridge in said inner bearing in order to snap into said groove while said second flange butts against the distal end of each leaf when said locking ring is pushed over the outer wall of said inner bearing, preventing the leaves of said bearing from moving outward and thereby releasably locking said bearing around said femoral head, there being an annular gap left between said lip of the locking ring and the adjacent periphery of the metal shell, whereby said locking ring may be readily disengaged and said femoral head removed while leaving said bearing fixedly secured within said shell by prying said lip away from said shell periphery.

2. A cup assembly according to claim 1, in which said plastic is ultra high molecular weight polyethylene.

3. A cup assembly according to claim 1, in which said metal is a high strength chromium-cobalt-molybdenum alloy.

4. A cup assembly according to claim 3, in which the outer surface of said metal shell is highly polished.

5. A cup assembly according to claim 1, in which the first flange of the locking ring is a circular flap which lockingly engages with the groove in said inner bearing.

6. A cup assembly according to claim 5, in which the inner surface of said locking ring has an additional convex flange, located above said second flange, which convex flange engages with a cooperating concave groove in the outwardly projecting lip at the distal end of each leaf of said inner bearing.

* * * * *